United States Patent [19]

Giaever

[11] 3,960,491
[45] June 1, 1976

[54] METHOD AND APPARATUS FOR DETECTING IMMUNOLOGICALLY REACTIVE BIOLOGICAL PARTICLES

[75] Inventor: Ivar Giaever, Schenectady, N.Y.
[73] Assignee: General Electric Company, Schenectady, N.Y.
[22] Filed: Apr. 1, 1974
[21] Appl. No.: 457,094

[52] U.S. Cl. .......................... 23/230 B; 23/253 R; 23/253 TP; 23/259; 195/103.5 R; 195/127; 424/12
[51] Int. Cl.² ........................................ G01N 33/16
[58] Field of Search ............. 23/230 B, 259, 253 R; 424/12; 195/103.5 R, 127

[56] References Cited
UNITED STATES PATENTS

| | | | |
|---|---|---|---|
| 3,390,962 | 7/1968 | Goldsmith | 424/12 X |
| 3,674,438 | 7/1972 | Shen | 23/230 B |
| 3,692,491 | 9/1972 | Trentelman | 23/230 B X |
| 3,709,661 | 1/1973 | Hubscher | 23/230 B X |
| 3,718,436 | 2/1973 | Ushakoff | 23/253 R |
| 3,725,004 | 4/1973 | Johnson | 23/230 B |
| 3,853,467 | 12/1974 | Giaever | 23/230 B |

Primary Examiner—Morris O. Wolk
Assistant Examiner—Sidney Marantz
Attorney, Agent, or Firm—Leo I. MaLossi; Joseph T. Cohen; Jerome C. Squillaro

[57] ABSTRACT

A metallized solid substrate is covered with a moistened porous paper, and specimens of first and second solutions suspected of respectively containing first and second immunologically reactive biological particles specific to each other are applied to selected areas of the paper and allowed to diffuse therein. Presence of the first and second biological particles in the solutions is indicated with high sensitivity by formation of a complexed protein precipitate line on the metallized substrate along the region of intersection of the two diffused particles and which is visible with good contrast to the unaided eye.

23 Claims, 4 Drawing Figures

METHOD AND APPARATUS FOR DETECTING IMMUNOLOGICALLY REACTIVE BIOLOGICAL PARTICLES

My invention relates to a method and apparatus for detecting with the unaided eye with high sensitivity and obtaining a durable record of an immunological reaction on a solid substrate surface, and in particular, for detecting the reaction as the result of a double diffusion in a suitable cellulose acetate membrane and without having to utilize a staining process.

This application is related to my concurrently filed applications Ser. No. 457,093 entitled "Method and Apparatus for Detecting Immunologic Reactions by Diffusion in Gel," Ser. No. 457,092 entitled "Method and Apparatus for Determination of Concentration of Immunologically Reactive Biological Particles", and Ser. No. 457,091 entitled "Method and Apparatus for Quantitative Surface Inhibition Test" as well as to my co-pending applications Ser. No. 266,278 entitled "Method and Apparatus for Detection and Purification of Proteins and Antibodies" filed June 26, 1972, now abandoned; Ser. No. 384,113 entitled "Improved Method and Apparatus for Detection and Purification of Proteins and Antibodies" filed July 30, 1973, now abandoned, and Ser. No. 445,204 entitled "Improved Substrate for Immunological Tests and Method of Fabrication Thereof" filed Feb. 25, 1974 and assigned as herein.

Immunological reactions are highly specific biochemical reactions in which a first immunologically reactive biological particle (generally protein) known as the antigen, combines (links) with a second protein specific to the antigen and known as the antibody, to form an immunologically complexed protein. Immunological reactions taking place within a biological system, such as an animal or human being, are vital in combatting disease. In a biological system, the entry of a foreign protein, i.e., the antigen, causes the biological system to produce the specific antibody proteins to the antigen in a process not fully understood at this time. The antibody protein molecules have available chemical combining or binding sides which complement those of the antigen molecule so that the antigen and antibody link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited co-pending applications disclose that an arbitrary protein will adhere to a substrate in a monomolecular layer only, and that no other arbitrary protein will adhere to the protein layer. On the other hand, the specificaly reacting protein to the first protein adsorbed onto the substrate will immunologically bond thereto. In accordance with the teachings of those applications, this discovery is exploited to provide medical diagnostic apparatus in which a slide having a monomolecular layer of one protein adsorbed thereon is used to test suspected solutions for the presence of the specifically reacting protein thereto. If the specifically reacting protein is present in the solution, the slide after exposure to the solution has a bimolecular protein layer thereon. If the specifically reacting protein be absent from the solution, the slide after exposure to the solution has only the original monomolecular layer thereon. Optical, electrical and chemical means for distinguishing between bimolecular and monomolecular biological particle layers are taught in the related co-pending applications and have different degrees of sensitivity and economy.

Because antibodies are produced by biological systems in response to invasions thereof by foreign proteins, the detection of antibodies in a biological system is of medical diagnostic value in determining the antigens to which the system has been exposed. A typical example of diagnostic detection of antibodies is the detection of antibodies to syphylis or gonorrhea in human serum. Conversely, the detection of certain antigens in a biological system also has medical diagnostic value; examples of diagnostic detection of antigens include detection of HCG protein molecules in urine as a test for pregnancy, and detection of hepatitis-associated-antigen (HCG) molecules in the blood of prospective blood donors.

In order to perform such diagnostic tests, the appropriate protein of the immunologically reacting pair must be obtained. The only known source of an antibody protein is a living biological system. More particularly only vertebrates are known at this time to exhibit immunological reactions to the introduction of a foreign protein. For example, many antibodies are found in the blood serum of animals and human beings which have been exposed to the corresponding antigens. Many antigens, however, may be controllably produced in laboratory cultures. However, some antigens, for example hepatitis-associated-antigens, are at present, like antibodies, only obtainable from the higher living biological systems.

It is known in the immunological art that antibody molecules function as antigens when introduced into the system of a vertebrate to whom they are foreign proteins.

Accordingly, specifically reacting antibodies to a given antibody may be readily produced in such vertebrate system.

As presently practiced, both the collection and purification, and the diagnostic utilization of immunologically reactive biological particles rely upon the precipitating or agglutinating characteristic of the proteins resulting from the immunological complexing reaction. The classic example of these diagnostic uses is the blood typing procedure in which blood samples are mixed with serum antibodies and blood type is determined by observing any agglutination occurring in the blood samples.

Another diagnostic utilization of immunologically reactive biological particles is the HCG protein pregnancy test which is currently practiced as an inhibition test. The test is performed by mixing a quantity of anti-HCG serum into a urine specimen. A plurality of polystyrene spheres which have been coated with HCG protein are then introduced into the previously prepared urine specimen. The polystyrene spheres will agglutinate if, but only if, an HCG protein is absent from the urine specimen. If HCG protein is absent from the urine specimen, the HCG protein on the polystyrene spheres complexes with the antiHCG serum previously introduced into the urine specimen and the spheres agglutinate. If, on the other hand, HCG protein is present in the urine specimen, it complexes with the previously introduced anti-HCG serum so that the introduced anti-serum is not available to complex with the HCG protein on the spheres to cause agglutination thereof. Further, in the case of other type protein diagnostic tests such as for the detection of hepatitis-associated antigen, it would also be highly desirable to obtain a more sensitive test. The shortcoming of agglutination tests is that the particles involved may tend to agglomerate for any of a variety of reasons having nothing to do with immunological agglutination, thereby decreasing the reliability of the test. Typically, agglutination tests are performed with great care by skilled technicians, but nevertheless occasional diagnostic errors occur.

Double diffusion immunologic experiments have been carried out in the prior art on cellulose acetate membranes and in gels in which specimens containing antigens and their antibodies are applied to different areas of the wet membrane (or wells in the gel) and diffuse toward each other to form a complexed protein precipitate line. However, in such prior art experiments, the sensitivity of the test was not as high as might often be desired, and the precipitate line was not visible to the unaided eye until the cellulose acetate membrane or gel was suitably stained with a protein material such as Amido Black as described in the book "Methods in Immunology and Immunochemistry," Volume III, edited by C.A. Williams and M.W. Chase, Academic Press, pages 153 and 169. This staining process adds another step in the method for detecting such biological particles. Further, the use of gel has the disadvantage in that undesired bacteria growth readily develops in the gel during the time it is stored.

Finally, although the substrates (slides) described in my hereinabove-referenced patent applications are satisfactory in their performance for detecting a bimolecular layer of immunologically reactive biological particles, such substrates are not, by themselves, well adapted for the double diffusion technique described hereinabove. This result also occurs with another type of metallized slide known in the prior art, the anodized tantalum slide described in the articles "Interactions Among Human Blood Proteins at Interfaces," authors L. Vroman et al, Federation Proceedings, volume 30, No. 5 (September-October, 1971) pages 1494–1502 and "Three Simple Ways to Detect Antibody-Antigen Complex on Flat Surfaces," authors A. L. Adams et al., Journal of Immunological Methods 3 (1973) pages 227–232, which is, however, less sensitive than my indium-gold alloy, indium oxide slide disclosed and claimed in my above-referenced co-pending application Ser. No. 445,204, especially in the detection of hepatitis. Another article related to prior art metallized slides is "Immunologic and Enzymatic Reactions Carried Out at a Solid-Liquid Interface," by Alexandre Rothen, Physiological Chemistry and Physics 5 (1973) pages 243–258.

Therefore a principal object of my invention is to provide a simple method and apparatus for detecting immunologically reactive biological particles with a significantly higher sensitivity than is obtained with conventional double diffusion techniques.

Another object of my invention is to provide an improved method and apparatus for the double diffusion detection of immunological reactions utilizing a cellulose membrane as the diffusing medium.

Another object of my invention is to provide a simple method and apparatus for detecting immunologically reactive biological particles by a double diffusion process without the need for staining the cellulose acetate membrane in which specimens of solutions of the particles diffuse.

A further object of my invention is to provide a simple method and apparatus for producing a durable record of the precipitate line formed by immunological reaction between the particles which is visible to the unaided eye with good contrast.

Briefly, and in accordance with the objects of my invention, I provide a method and apparatus for detecting second immunologically reactive biological particles in a test solution by direct visual observation of a complexed protein precipitate line formed on a metallized slide as a result of an immunologic reaction. The metallized slide is initially covered with a moistened cellulose membrane. Then, a specimen of a first solution containing first immunologicaly reactive biological particles is deposited on a first selected area of the moist membrane, and a specimen of a test solution suspected of containing second biological particles which are specific to the first particles is deposited on a second selected area spaced from the first, and the two specimens are allowed to diffuse. During the diffusion process, the biological particles permeate the membrane thickness and a complexed protein precipitate line forms at the intersection of the diffusing first and second biological particles at the surface of the metallized solid substrate. The precipitate line is visible with good contrast to the unaided eye without requiring the use of a staining material and forms a durable record of the detected immunologic reaction. The apparatus of the metallized solid substrate and moistened membrane is maintained in a moist chamber during the diffusion process and obtains the detection of the second biological particles in an amount as small as $10^{-9}$ grams which is a sensitivity approximately two orders of magnitude better than that which can be obtained with any of the conventional double diffusion techniques.

The features of my invention which I desire to protect herein are pointed out with particularity in the appended claims. The invention itself, however, both as to its organization and method of operation together with further objects and advantages thereof, may best be understood by reference to the following description taken in connection with the accompanying schematic drawing wherein:

Figure 1A:
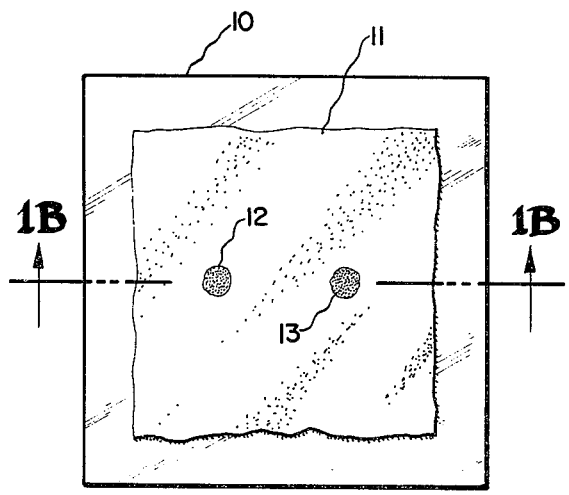
FIG. 1A is a plan view of the apparatus in accordance with my invention at the time two drops of solutions which may contain biological particles are deposited on the cellulose acetate membrane.
Figure 1B:
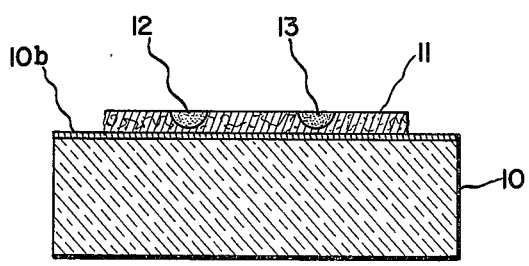
FIG. 1B is an elevation view, in section, of the apparatus illustrated in FIG. 1A taken along line 1B—1B.

Referring now to FIGS. 1A and 1B, there are shown the apparatus, in accordance with my invention, for detecting immunologically reactive biological particles as a result of an immunological reaction thereof occurring on a solid substrate surface. In particular, the apparatus consists of a metallized substrate 10 and a moistened cellulose membrane 11 which covers at least a portion of the metallized surface of the substrate member. Substrate 10 has a substantially flat top surface and is fabricated of a suitable material which may be a metal, glass, plastic or similar material. Substrate 10 is preferably in the form of a glass slide such as a conventional microscope cover glass that is readily commercially available. The top flat surface of substrate 10 is metallized in accordance with the teachings disclosed in my above-identified patent applications which are hereby incorporated by reference herein. As examples of such teachings, the metallization may consist of (1) a noncontinuous layer, i.e., metal particles or globules with indium being a typical metal, or (2) a first layer of the indium globules overlaped with a thin gold film, or (3) a layer of the indium globules (or a constant thickness continuous layer of indium) overlapped with a thin film of gold which is alloyed with the indium and a thin oxide film of the thereover indium, or (4) a metal such as nickel and oxide film thereof. The indium particle metallization is often a preferred embodiment for generally equal size biological particles whereas the indiumgold alloy and indium oxide coated substrate is often a preferred embodiment for very differently sized particles such as when testing for hepatitis. Following the teaching in the above-referenced patent applications, the non-continuous layer of indium particle metallization requires use of a light-transmissive substrate material such as glass or plastic, and the indium particles evaporated on the substrate surface have diameters on the order of 1000 Angstrom although the precise size of the particles is not critical as long as they have diameters equal to a large fraction of a wavelength of visible light. The color of the indium particle metallization is a light brown. In the case of the indium-gold alloy, indium oxide metallization, the thickness of the indium is approximately twice the thickness of the gold when initially deposited (indium thickness is approximately 2000 A, gold is approximately 1000 A,) and the indium oxide film is several hundred Angstrom to obtain a bronze color of such film. As noted in my patent application Ser. No. 445,204, the degree of oxidation of the first metal determines the color of the oxidized film so that various degrees of oxidation produce different colored slides having different sensitivities for different thicknesses of the layers of the biological particles.

In the case of the metallized coating 10b on the top surface of substrate 10 being formed of globules of indium, or the indium-gold alloy, indium oxide film, the top surface of such metallized coating is slightly irregular. Altenatively, such metallized coating when formed with a continuous, constant thickness layer of the indium, film of gold and the indium oxide, has a top surface that is substantially flat. Either type of metallized substrate 10 may be utilized in my invention depicted herein. The cellulose membrane 11 is a suitable, very thin membrane of cellulose or a cellulose derivative such as cellulose acetate, and may be any porous paper such as any of the common filter papers or simply a tissue paper. The dimensions of membrane 11 may be the same as, or different from that of substrate 10. Membrane 11 is as thin as can conveniently be used, and is less than one millimeter thick and less than the thickness of the paper used in prior art double diffusion techniques. In a typical application, and for convenience in depicting my apparatus, membrane 11 is illustrated as being of smaller length and width dimension than substrate 10. Substrate 10 may be as small as a half inch square. Further details of the substrate metallization and fabrication thereof are disclosed in my above-referenced patent applications which are hereby incorporated by reference herein.

Cellulose membrane 11 may be moistened either before or after it is placed on substrate 10. Membrane 11 should be placed on the metallized surface smoothly with sufficient care such that it is in contact with the metallized surface along its entire bottom surface. The wet membrane covered substrate assembly is then placed in a moist chamber and a specimen of a first solution containing first immunologically reactive biological particles is deposited on a first selected area of the moist membrane 11. As illustrated in FIGS. 1A and 1B, the specimen of the first solution may consist of a single drop 12 as a typical example. Immediately after the drop 12 of the first solution is deposited on membrane 11, or at the same time, a specimen such as a drop 13 of a test solution suspected of containing second immunologically reactive biological particles which are specific to the first particles is deposited on a second selected area of membrane 11 spaced from the first and the two specimens are allowed to diffuse in the membrane. FIGS. 1A and 1B illustrate the apparatus at the moment drops 12 and 13 have just permeated into membrane 11.

Figure 2A:
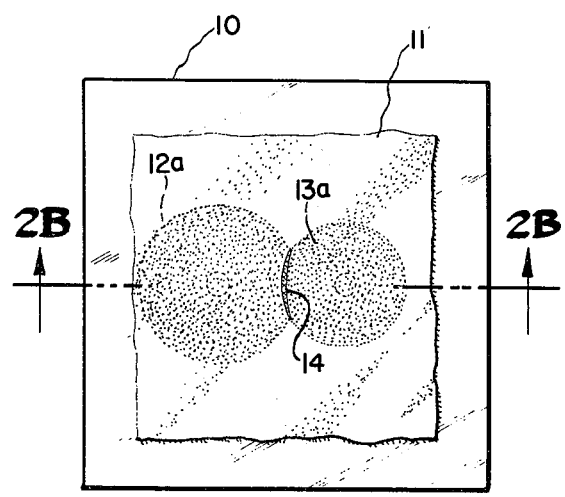
FIG. 2A is a plan view of the apparatus of FIG. 1A after diffusion of the two drops and formation of the precipitate.
Figure 2B:
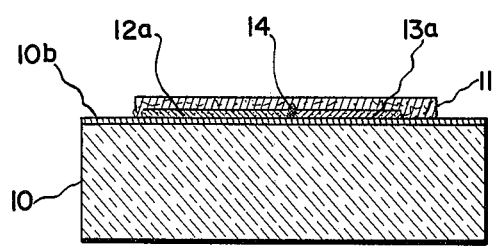
FIG. 2B is a plan view, in section, of the apparatus illustrated in FIG. 2A taken along line 2B—2B.

The first and test solutions generally also contain other (nonspecific) biological particles, a typical example being a first solution of rabbit anti-serum and a test solution of human serum. During the diffusion of specimens 12 and 13 in the cellulose acetate membrane 11, the first and other (nonspecific) biological particles in specimen 12 permeate the membrane thickness and are adsorbed onto the surface of the metallized slide to form a monomolecular layer 12a of such particles thereon as illustrated in FIGS. 2A and 2B. In like manner, any second and other (nonspecific) particles in the second specimen permeating the membrane thickness are adsorbed onto the surface of the metallized slide to form a monomolecular layer 13a of such particles thereon. Along the region of intersection of the diffusing first and second particles there is formed a complexed protein precipitate line 14 which is several layers thick and results from an immunologic reaction of the first and second particles. The diffusion of single drops 12, 13 of the solutions in the moist membrane 11 is radially outward to form circular patterns such that precipitate 14 is a straight or curved line depending on the types of particles and concentrations thereof. The time for completion of the diffusion and formation of the precipitate line is a function of the types of first and second biological particles involved, the concentration of each particle in its respective solution, the temperature and the spacing of drops 12 and 13 on membrane 11. Thus, a close spacing of the two drops results in the two diffusions intersecting more rapidly and thereby forming the precipitate line 14 more rapidly than if the drops are spaced further apart. The drops may be spaced apart as little as several millimeters. The time for diffusion of the specimens and formation of the precipitate line is generally several hours, although the process can be speeded up to several minutes if electrophoresis is employed. The moistening agent in membrane 11 can be distilled water, a salt solution or a buffered solution such that it will be nonreactive with the specimens and such moisture is held immobile so that a controlled diffusion of the specimen occurs in the membrane to thereby obtain reproducible results.

After formation of the precipitate line 14 on the metallized surface of substrate 10, the cellulose membrane 11 is peeled from the substrate surface and the substrate surface with the precipitate 14 adhered thereon is rinsed, typically with distilled water, and dried preferably by blowing air at room temperature across the substrate. The metallized surface of substrate 10 is then visually examined. The examination is a direct visual observation in that the unaided eye is employed to observe the light reflected off or transmitted through the metallized surface of the substrate. The indium particle slide is viewed by transmitted light whereas the indium-gold alloy, indium oxide film slide is viewed by reflected light. The color of the precipitate depends on the color of the slide metallized surface. Thus, in the case of a bronze color indium oxide film, the precipitate is a purplish line, and in the case of the indium slide a darker shade of brown.

The complexed protein precipitate line 14 is visible with good contrast to the unaided eye and results in the detection of biological particles to a sensitivity which is at least two orders of magnitude better than that which can be obtained with conventional double diffusion techniques. As an example, I have detected bovine serum albumin (BSA) antibodies in the amount of $10^{-9}$ grams which to my knowledge is two orders of magnitude better than that obtained with the other simple double diffusion techniques. This detection of an amount of $10^{-9}$ grams is not believed to be a maximum sensitivity capability of my apparatus since the conditions were not optimized in that particular test.

The sensitivity of my apparatus is substantially higher than the sensitivity of other conventional double diffusion techniques such as described in the above-referenced book "Methods in Immunology and Immunochemistry," volume III, since only a very small amount of the biological particles are necessary to be present in order to be detectable as described hereinabove.

A further advantage of my invention is that the precipitate line 14 on the metallized surface of substrate 10 forms a durable record of the detected immunological reaction. Finally, no staining of the precipitate is required, as distinguished from the prior art double diffusion techniques, in order to visually detect the precipitate, and the contrast is also significantly better than that obtained with the prior art techniques.

In the detection method described hereinabove, it was assumed that the first solution was a known solution containing the first biological particles. Alternatively, both the first and second solutions may be test solutions suspected of containing the first and second particles in which case formation of the precipitate line would indicate that such particles were, indeed, contained within the respective solutions whereas absence of the precipitate line would merely indicate that one or both of the solutions did not contain their respective particles. In the case of the known solutions containing the first particles, such first particles may be produced in laboratory cultures or obtained from the higher living biological systems as described hereinabove, and are commercially available in highly purified form, and if not available commercially, may be purified chemically. The solution of the first biological particles may be a salt solution of water or other liquid appropriate to, and not reactive with, the first biological particles, or a human serum sample, as a typical example.

The biological particles referred to hereinabove as first and second biological particles may be antigens, antibodies, viruses, bacteria, hormones, enzymes or other particles which can be readily grown or otherwise isolated and collected or are present in human serum or other solution being tested. A typical example of particular biological particles which are detected by the method and in the apparatus described hereinabove is hepatitis B antigen (HBA$g$) as the first biological particles and antibodies to hepatitis HBA$b$) as the second biological particles.

In many cases, the specimen 12 of the first particles will be a specimen containing the particular antigens such as HBA$g$. In such case, the test solution would be a drop of human serum taken from a patient suspected of having had hepatitis B, and in a direct test therefore, the presence of antibodies (HBA$b$) would be detected by direct visual observance of precipitate line 14. Alternatively, the particles in the first specimen 12 can be antibodies to a particular disease, and in a direct test, the presence of antigens to such antibodies in the serum sample would be determined by my detection test.

An indirect or inhibition test for the detection of particular immunologically reactive biological particles may also be conducted with my apparatus. The principle of the inhibition test is that the first particles, if present in sufficient quantity, will neutralize free second particles in solution. Thus, in the inhibition test, HBA$g$ particles, if present in sufficient quantity, will neutralize free antibodies to hepatitis B in solution. This reaction will prevent the antibodies from forming observable complexes with HBA$g$ when the test specimen is deposited on the cellulose membrane. The inhibition test for an antigen, and specifically HBA$g$ is accomplished as follows: A drop of known solution of HBA$g$ is deposited as drop 12 on the cellulose membrane 11 and the HBA$g$ and other particles present in the solution are adsorbed as a monomolecular layer 12$a$ on the metallized surface of substrate 10 as in the direct test described hereinabove. The test solution is prepared by adding a human serum sample to be tested to a solution of HBA$b$ in a vial or other suitable container. The vial is then stored for a time interval sufficient for the HBA$b$ to complex with HBA$g$ in the human serum sample, if the antigen is present therein. The vial is preferably agitated to increase the rate of complexing. Finally, a drop 13 of the test solution is deposited on the cellulose membrane 11, and after a suitable period of time for the diffusion of specimens 12 and 13, membrane 11 is peeled from the substrate 10 and the metallized surface of substrate 10 is visually examined. The results of the inhibition test are the opposite of the direct test, that is, presence of HBA$g$ in the human serum sample produces no precipitate line 14 whereas presence of such precipitate line indicates absence of HBA$g$ in the human serum sample.

The inhibition test for the detection of HBA$b$ is performed similarly to the inhibition test for HBA$g$ with the obvious substitution of the antigen for antibody and antibody for antigen in each of the steps.

In the above hepatitis tests, the HBA$b$ may be obtained from human serum of a patient known to have had hepatitis B, or it may be developed in a goat, rabbit or other suitable animal by injection thereof with the HBA$g$, waiting a suitable incubation period such as two weeks, and then drawing blood containing the specific antibody from the animal and separating the antibody from the remaining blood particles.

From the foregoing description, it can be appreciated that my invention makes available an improved double diffusion method and apparatus for detecting immunologically reactive biological particles in a test solution by direct visual observation of the metallized surface of a solid substrate on which a complexed protein precipitate is formed as a result of an immunological reaction between first biological particles and the particular biological particles being investigated and which are specific to the first particles. My method and apparatus are very simple in that only a moistened cellulose membrane is required to be placed on the surface of the substrate for diffusion of the specimens and the unique and highly sensitive properties of my metallized substrate thereby avoids the need for staining the cellulose membrane or substrate in order to detect the precipitate line by direct visual observation. The cellulose membrane used in my apparatus can be considerably thinner than that used in the prior art since it is used only for diffusion of the specimens whereas the prior art requires a substantial thickness in order to form the precipitate line therein (although a slight precipitate line also forms in my cellulose membrane). My detection method is much more sensitive than other conventional simple double diffusion methods for detecting immunologically reactive biological particles and has detected BSA antibodies in the amount of $10^{-9}$ grams as one example, and is capable of even higher sensitivity. As a result, I have provided a simple method wherein the previously described metallized slide described in the hereinabove-referenced patent applications can now be adapted for use with a double diffusion of specimens in a cellulose membrane for detecting the biological particles. Since the metallized slides can be fabricated repetitively with identical characteristics, the results of the detection of the biological particles in accordance with my present invention are very consistent and can serve many useful purposes, especially in the medical diagnostic field in the analysis of human serum, for example, for the detection of various antibodies and antigens therein. Since the visual contrast between the precipitate line and monomolecular layer of biological particles is very distinct when utilizing my metallized slide, the detection is accomplished by direct observation with the unaided eye and therefore does not require elaborate test equipment and obtains the precipitate line in durable form.

Having described my invention with reference to a specific embodiment, it is believed obvious that modification and variation of my invention is possible in the light of the above teachings. Thus, the shape and size of the substrate and cellulose membrane may be varied and virtually any pair of immunologically reactive biological particles which will immunologically react with each other can be detected with my apparatus. Further, my metallized substrate, if sufficiently large, can be employed to detect the presence of the second biological particles in more than one test solution by depositing the specimens thereof in separate selected areas on the moist cellulose membrane surrounding a central area on which the specimen known to contain the first particles is deposited. The presence of the second particles in each test solution is then detected by observing the formation on the metallized substrate of precipitate lines formed by the first particles in the central diffusion immunologically reacting with the second particles in the respective surrounding diffusions. A measure of the concentration of the second particles in the test solutions can also be obtained in this manner if one of the second solutions (i.e. a standard solution) contains a known concentration of the second particles. A good approximation of the concentration can be estimated by comparing the relative position of each precipitate line (relative to the distance between depositions of the first particle specimen and each test solution specimen) to that of the relative position of the precipitate line formed by the standard solution specimen. Further, metallizations other than the indium and the indium-gold alloy, indium oxide may be found to obtain better contrast of the precipitate line on the metallized surface for some specific biological particles. Also, the irregular surfaced embodiment for my metallized slide could obviously also be fabricated by starting with an irregular surfaced substrate and evaporating constant thickness layers of a metal such as indium thereon. Finally, it should be evident that my apparatus may also be utilized for determining the concentration of the second biological particles by first adsorbing a monomolecular layer of the first biological particles along substantially the entire metallized surface of substrate 10, and then placing the moistened cellulose membrane 11 on top of the first particle layer in complete contact therewith. The specimen of the test solution is then deposited on a first selected area of the moist membrane, and diffusion of such specimen results in an immunologic reaction whereby a monomolecular layer of the second biological particles is formed on top of the first particle layer in the shape of a small circular spot if the test solution contains such second particles. The diameter of the second layer spot, which is visible with good contrast to the unaided eye as a purplish spot in the case of a bronze color metallized slide, is related to the concentration of the second particles in the test solution. Thus, in the conduct of this variant method, coating 10b on substrate 10 would represent both the metallization and monomolecular layer of first biological particles, 12 is a drop of a first test solution, 13 is a drop of a second test solution or a standard solution (i.e., solution of known concentration of the second particles) and 12a and 13a are the circular spot monomolecular layers of the second particles. Thus, my apparatus as fabricated may also consist of a metallized substrate with a monomolecular layer of particular first immunologically reactive biological particles adhered thereto and a cellulose acetate disposed thereon. After formation of the second layer spot(s), the membrane is peeled off, the metallized slide is dried, and then visually examined with the unaided eye and the diameter(s) of the second layer spot(s) is measured (and compared to a standard) for determining the second particle concentration. It is, therefore, to be understood that changes may be made in the particular embodiment of my invention as described which are within the full intended scope of the invention as defined by the following claims.

What I claim as new and desire to secure by Letters Patent of the United States is:

1. Apparatus for determining the presence or absence of select biological particles in a biological sample, comprising in combination
    a solid substrate member having a metallized surface area thereon and
    means for locating a layer of immobilized liquid on and in direct contact with said metallized surface area, said locating means being a porous membrane of a material selected from the group consisting of cellulose and cellulose derivatives, said porous membrane containing said liquid.
2. The apparatus set forth in claim 1 wherein the substrate member is formed of a light-transmissive material selected from the group consisting of plastic and glass.

3. The apparatus set forth in claim 1 wherein the metallized surface area of the substrate member is a non-continuous film consisting of metal particles.

4. The apparatus set forth in claim 1 wherein the metallized surface area of the substrate member is formed from an alloy of two metals.

5. The apparatus set forth in claim 1 wherein the metallized surface area of the substrate member is formed from a metal and an oxide film thereof.

6. The apparatus recited in claim 1 wherein the liquid is aqueous.

7. The apparatus recited in claim 6 wherein the aqueous liquid is distilled water.

8. The apparatus set forth in claim 1 wherein the metallized surface area of the substrate member is formed from an alloy of two metals and has an outer oxide film of one of the two metals.

9. The apparatus set forth in claim 8 wherein the two metals are indium and gold and the oxide film is an indium oxide film.

10. The apparatus set forth in claim 9 wherein the surface of the substrate member beneath the metallized surface area is flat and the metallized surface area is slightly irregular.

11. The apparatus set forth in claim 9 wherein the surface of the solid substrate member beneath the metallized surface area is flat and the metallized surface area is flat.

12. A method for determining the presence or absence of select biological particles in a biological sample, comprising the steps of:
   disposing a layer of liquid immobilized in a porous membrane of a material selected from the group consisting of cellulose and cellulose derivatives, said porous membrane being in direct contact over all the underside thereof with said metallized surface,
   placing a quantity of solution containing biological particles immunologically specific to said select biological particles in contact with a first selected area of said porous membrane,
   placing a quantity of biological sample in contact with a second selected area of said porous membrane spaced from said first selected area,
   preventing desiccation of said layer during diffusion of said quantities of solution and biological sample through the immobilized liquid to said metallized surface beneath said porous membrane,
   removing said porous membrane and
   inspecting the exposed surface to determine the presence or absence of complexed precipitate line adhered to said metallized surface between positions thereon in juxtaposition with said first and second selected areas.

13. The method set forth in claim 12 wherein first and second selected areas are spaced apart in the order of several millimeters.

14. The method recited in claim 12 wherein the select biological particle is an antigen and the biological particle specific thereto is an antibody.

15. The method recited in claim 12 wherein the metallized surface contains oxide of a metal present in the metallized surface.

16. The method recited in claim 12 wherein the metallized surface is irregular.

17. The method recited in claim 12 wherein the metallized surface is substantially flat.

18. The method recited in claim 12 wherein the inspecting step is conducted by means of light transmitted through the metallized surface.

19. The method recited in claim 12 wherein the layer of liquid immobilized in the porous membrane is formed with the said porous membrane in place on the metallized surface.

20. The method recited in claim 12 wherein the liquid is aqueous.

21. The method recited in claim 20 wherein the aqueous liquid is distilled water.

22. The method recited in claim 12 wherein a plurality of separate quantities of different biological samples are placed in contact with separate selected areas of the porous membrane.

23. The method recited in claim 22 wherein one of the plurality of quantities is a quantity of a standard solution containing a known concentration of select biological particles therein to produce a standard precipitate line.

* * * * *